United States Patent [19]

Sevenet et al.

[11] 3,937,709

[45] Feb. 10, 1976

[54] VINCAMINE DERIVATIVES AND PROCESS FOR THE PREPARATION OF VINCAMINE AND DERIVATIVES THEREOF

[75] Inventors: Thierry Sevenet, Gif, Yvette; Claude Thal, Malakoff; Henri Philippe Husson, Chevreuse; Pierre Potier, Bois-Darcy, all of France

[73] Assignee: Agence Nationale de Valorisation de la Recherche (ANVAR), Neuilly-sur-Seine, France

[22] Filed: June 15, 1973

[21] Appl. No.: 370,334

[30] Foreign Application Priority Data
June 19, 1972 France .............................. 72.22021

[52] U.S. Cl. ....... 260/293.53; 424/267; 260/239.3 P
[51] Int. Cl.² ..................................... C07D 471/04
[58] Field of Search ................................ 260/293.53

[56] References Cited
UNITED STATES PATENTS

| | | | |
|---|---|---|---|
| 3,454,583 | 7/1969 | Kuehne ............................. | 260/294.3 |
| 3,755,335 | 8/1973 | Thal et al. ......................... | 260/293.53 |
| 3,830,823 | 8/1974 | Castaigne .......................... | 260/293.53 |

*Primary Examiner*—G. Thomas Todd
*Attorney, Agent, or Firm*—Eric P. Schellin

[57] ABSTRACT

New compounds having the formula

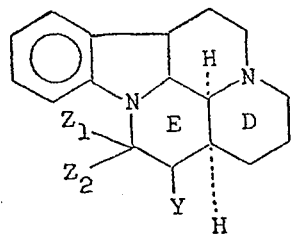

in which Y represents a hydrogen atom, in which case $Z_1$ and $Z_2$ represent simultaneously an oxygen atom, or $Z_1$ represents a methoxycarbonyl radical and $Z_2$ a hydroxy radical, or Y and $Z_2$ form together a carbon-carbon bond and $Z_1$ is a methoxycarbonyl radical, said compounds being additionally characterized by a cis-fusion of the D/E rings. Said new compounds and vincamine and certain of its derivatives are prepared from an enamine having the formula:

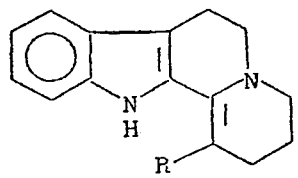

in which R is H or $C_2H_5$.

7 Claims, No Drawings

VINCAMINE DERIVATIVES AND PROCESS FOR THE PREPARATION OF VINCAMINE AND DERIVATIVES THEREOF

This invention relates to new vincamine derivatives and to a novel process for the preparation of vincamine and of vincamine derivatives.

It is known that vincamine possesses highly useful therapeutic properties and that it may be used for the treatment of cerebral vascular conditions.

The chemical synthesis of vincamine has already been effected, for example by M. E. KUEHNE (J. Am. Chem. Soc., 1964, 86, 2946) and by K. H. GIBSON and J. E. SAXTON (Chem. Comm., 1969, 1490).

Both the above mentioned methods have various drawbacks, particularly in that they lead, at different stages, to a mixture of isomers and make it possible to obtain vincamine only with low yields.

According to the process of this invention, vincamine and its derivatives are prepared from an enamine (compound described by R. N. Schut and T. J. Leipzig, J. Het. Chem., 1966, 3, 101).

The new vincamine derivatives included within the scope of the invention have the general formula:

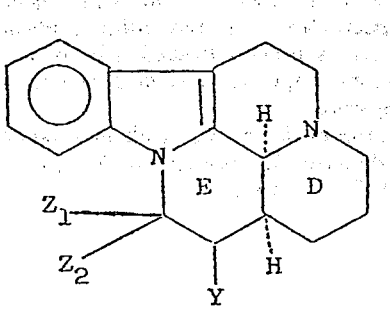

in which:

Y represents a hydrogen atom, in which case $Z_1$ and $Z_2$ represent simultaneously an oxygen atom, or $Z_1$ represents a methoxycarbonyl radical and $Z_2$ represents a hydroxy radical, or Y and $Z_2$ form together a carbon-carbon bond and $Z_1$ is a methoxycarbonyl radical, said compounds being additionally characterized by a cis-fusion of the D/E rings.

Said compounds are analogs of alkaloids of the deethyleburnane group.

The invention includes in particular within its scope 20-deethyl-vincamine, 20-deethyl-apovincamine and 20-deethyleburnamonine as their racemic and optically active forms.

The process for the preparation of vincamine and its derivatives which are described in the present application comprises condensing an enamine (1) with methyl α-bromomethyl-acrylate prepared according to the method disclosed by A. F. FERRIS (J. Org. Chem., 1955, 20, 780). The resulting immonium salt (2) is reduced with sodium borohydride to give compound (3). The group $>C=CH_2$ of compound (3) is oxidized in the presence of periodic acid with potassium permanganate or osmium tetraoxide according to the method disclosed by S. M. KUPCHAN (J. Org. Chem., 1962, 3103). The resulting ketone condenses immediately with the indole $>NH$ group to give compound (4) which is vincamine when R is ethyl or 20-deethyl-vincamine when R is H. On dehydration under acidic conditions, 20-deethyl-vincamine leads to compound (5), 20-deethyl-apovincamine.

Compound (4) may be reacted with lithium aluminum hydride within tetrahydrofuran and then with hot hydrochloric acid, to give compound (7).

Diagram I below illustrates the process for the preparation of said compounds

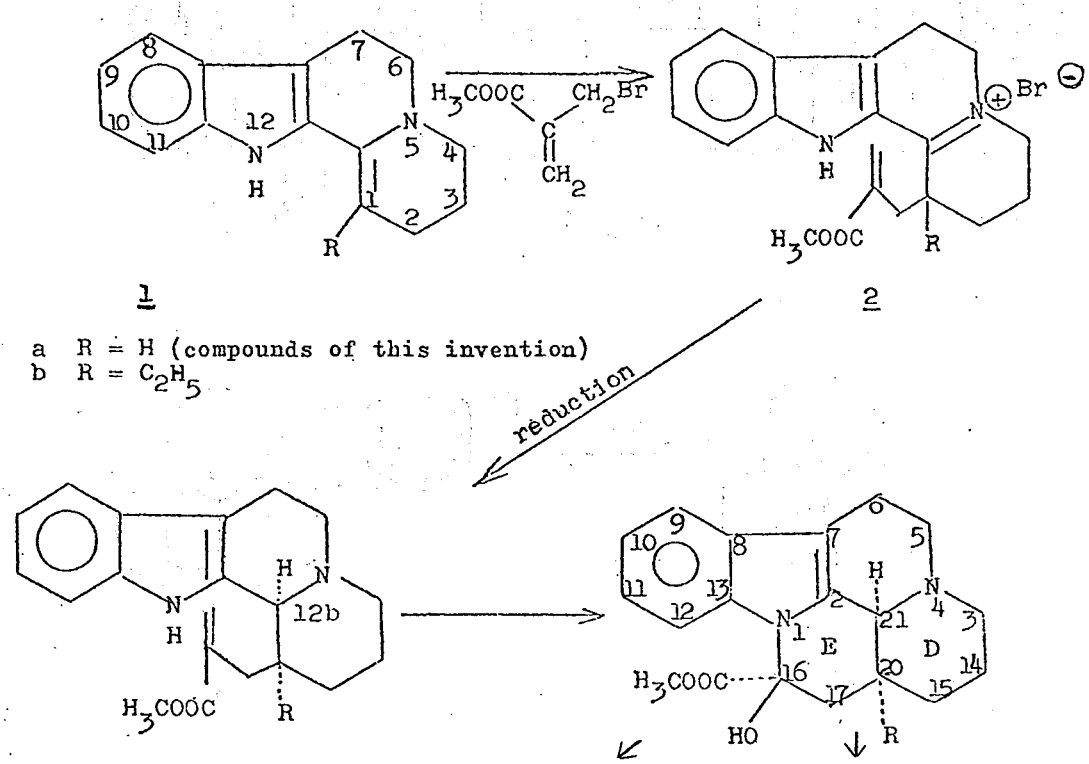

DIAGRAM I a  R = H (compounds of this invention)
b  R = $C_2H_5$

DIAGRAM I -continued

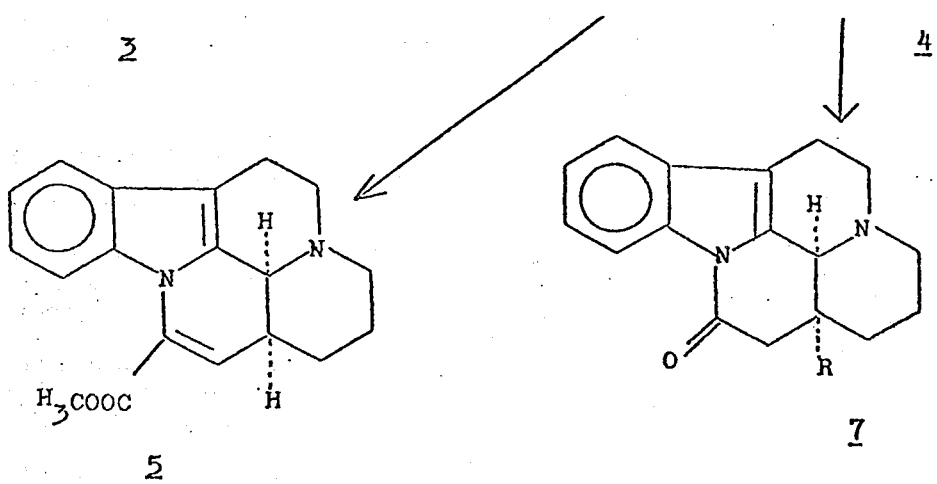

Amide (7) may also be prepared according to the reaction scheme illustrated below in Diagram II. Enamine (10) is alkylated with ethyl bromoacetate or iodoacetate, to give immonium salt (9) which is reduced with sodium borohydride or by hydrogenation in the presence of 10% palladium-over-charcoal, and resulting derivative (8) is then treated with sodium ethoxide in absolute ethanol or with potassium t-butoxide in anhydrous benzene, to give cis-quinolizidine derivative (7) in which the D/E rings are cis-fused.

The following examples illustrate the invention.

The melting points are determined with a Leitz microscope or with a Kofler block and are corrected; the NMR spectra are measured with a Perkin-Elmer type $R_{12}$ apparatus using tetramethylsilane as zero reference; the mass spectra are recorded with an AEI type MS9 apparatus.

For purposes of clarity, the alkaloid nomenclature is frequently used (J. Le Men and W. I. Taylor, Experientia, 1965, 21, 508).

DIAGRAM II

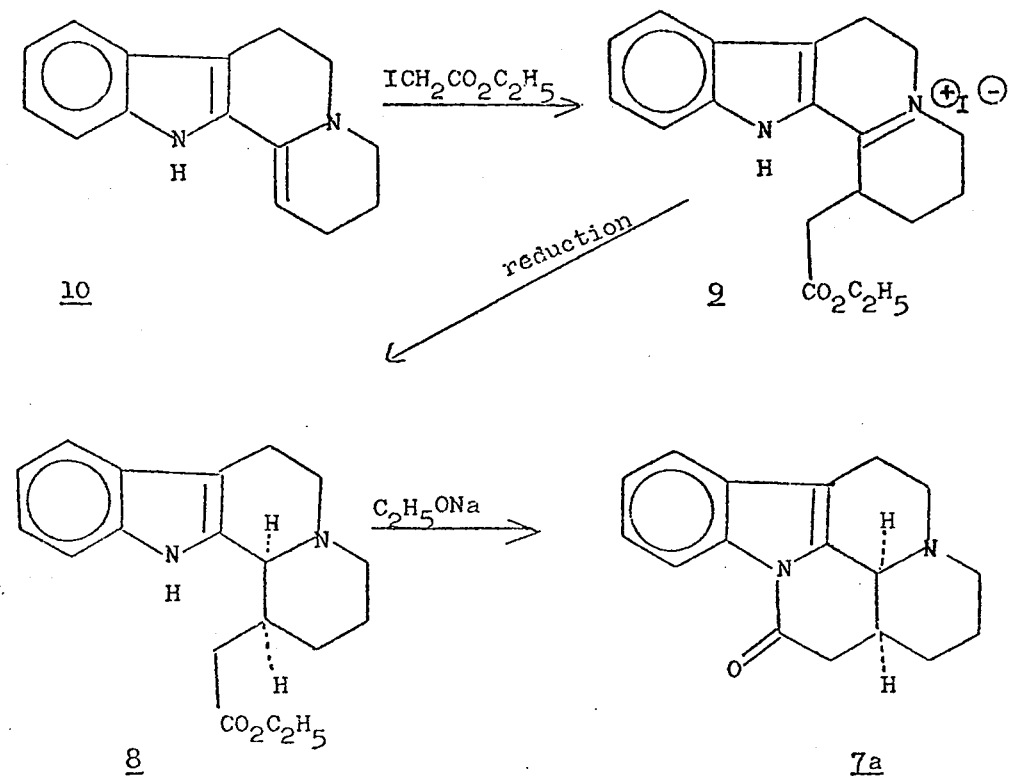

EXAMPLE 1

(DIAGRAM I)

a. 1,2,3,4,6,7,12,12b-Octahydro-1-(β-methoxycarbonylallyl)-indolo[2,3a]-quinolizine (Compound 3a, R = H)

1 g of enamine (compound 1, R = H) is dissolved in methanol (40 ml) in which a buffer mixture of disodium phosphate (3.6 g) and monosodium phosphate (1.4 g) is suspended.

Methyl α-bromomethylacrylate (2 ml) is added under a nitrogen atmosphere. The reaction mixture is stirred during 15 hours at room temperature, after which the inorganic phase is filtered off. Sodium borohydride is added to the filtrate, while cooling over an ice-bath. When reduction is complete (as ascertained by thin-layer chromatography), the material is poured into water and extracted with chloroform to give 1.2 g of a brown lacquer which is chromatographed through a silica column. The fractions eluted with benzene-ether (99:1) contain methyl α-bromomethylacrylate together with polyalkylated compounds.

Derivative (3a) (0.560 g) is separated as a colorless lacquer with benzene-ether 95:5.

I.R. Spectrum (CH Cl$_3$): 3460–3370 cm$^{-1}$ ($>$N—H), 2860-2810-2755 cm$^{-1}$ (Bohlmann's bands), 1715 cm$^{-1}$

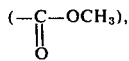

1630 cm$^{-1}$ ($>$C=CH$_2$)

U.V. Spectrum (EtOH): in neutral medium and in alkaline medium:
= 227 nm (log ε = 4.40), 276 nm (log ε = 3.79), 285 nm (log ε=3.81), 292 nm (log ε=3.74), 360 nm (log ε = 2.84), in acidic medium:
= 222 nm (log ε = 4.37), 274 nm (log ε = 3.82), 281 nm (log ε = 3.79), 2.91 nm (log ε = 3.68), 360 nm (log ε = 3.08).

Mass Spectrum: peaks at m/e 324 (M$^+$), 323, 309, 293, 265, 263, 249, 247, 225, 224, 197, 184, 170, 169, 144, 143, 96.

NMR Spectrum:
1 proton (N$_a$ —H) at 8.8 ppm
4 aromatic H's between 6.9 and 7.5 ppm
2 ethylenic H's: 2 doublets centered at 6.1 and 5.5 ppm (J = 2 Hz)
3 H (methyl ester); singlet at 3.70 ppm
1 H (C$_{12b}$) at 3.40 ppm.

The presence of Bohlmann's bands (2900-2700 cm$^{-1}$) in I.R. and the position of the signal, in nuclear magnetic resonance, of hydrogen (C$_{12b}$) at 3.40 ppm make it possible to contemplate a trans-quinolizidine linking of the C/D rings.

b. (±) 20-Deethyl-vincamine (Compound 4A, R = H)

Osmium tetraoxide (70 mg) is added to a solution of compound 3a (410 mg) in dioxan (145 ml) and water (45 ml).

After one hour of contact, with stirring, the medium turns black. Periodic acid (1.9 g) is added thereto.

The reaction mixture is stirred for a further 24 hours in the absence of light, after which potassium iodide and a normal sodium arsenite solution are added thereto until the material is decolorized and a pH of 7.5 is obtained. The reaction mixture is then extracted with chloroform to give 338 mg of a brown lacquer. Crystallization from acetone gives 150 mg of (±)-20-deethylvincamine (4a). M.p. (inst.) = 248°C (corr.).

Analysis: for C$_{19}$H$_{22}$O$_3$N$_2$ Calc. % : C 69.92 H 6.79 N 8.58
Found : C 70.21 H 7.09 N 8.10

Mass Spectrum : peaks at m/e 326 (M$^+$), 325, 311, 308, 267, 265, 264, 248, 238, 224, 209, 196, 180, 168, 167, 144.

I.R. Spectrum: (CH Cl$_3$): bands at 1740 cm$^{-1}$ (ester) and 3520 cm$^{-1}$ (OH)

U.V. Spectrum: maximum absorption at 229 nm (log ε = 4.44), 276 (3.88), 282 (3.89), 292 (3.74) in ethanol solution, and maximum absorption at 270 (3.93), 316 (3.53) in hydrochloric medium (11N).

N.M.R. Spectrum: After two minutes, there are noted:
4 aromatic protons between 7.6 and 7 ppm
1 3-proton singlet at 3.80 ppm representing the methyl ester.

The position of this signal is characteristic of the configuration contemplated at the level of carbon C$_{16}$.
1 broad signal at 5.1 ppm, characteristic of the proton at C$_{21}$ (this signal appears at 4.3 ppm in COCl$_3$).

after 4 hours of contact, due to a dehydration, appears the signal of the ethylenic proton carried by carbon 17 (doublet centered at 6.5 ppm J = 7 Hz). Corresponding product 5 was isolated.

Said spectra confirm the structure of compound 4a which possesses the stereochemistry of vincamine (compound 4b, R = C$_2$H$_5$) and, consequently, may be named (±)-deethyl-vincamine.

This compound is characterized by a cis-quinolizidine (C/D) linking and a cis-fusion of the D/E rings. Isomer 6a, having the formula:

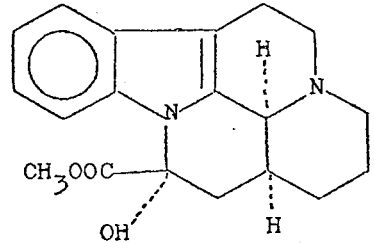

which is differentiated by the reverse stereochemistry at the level of carbon 16, could be isolated in the course of the purifications.

c. 20-Deethyl-apovincamine (compound 5)

This compound is obtained from 20-deethyl-vincamine (compound 4a) by dehydration in acidic medium.
IR Spectrum (CDCl$_3$): band at 1730 cm$^{-1}$ (ester); absence of OH band at 3520 cm$^{-1}$.

EXAMPLE 2

(±)-20-Deethyl-eburnamonine (Compound 7a, R = H). Diagram I.

To a mixture of compound 4a (20 mg) in tetrahydrofuran (10 ml) is added lithium-aluminum hydride (15 mg). After refluxing during 3 hours, the reaction mixture is evaporated, taken up into 2N HCl (5 ml) and is then heated during 3 hours over a boiling water-bath. The chloroform extract of the alkalinized reaction mixture gives, after evaporation, 17 mg of a brown lacquer which is chromatographed using a thick layer of silica, to give 3 mg of (±)-20-deethyl-eburnamonine, identified by its IR spectrum and by thin layer chromatography in various eluent mixtures (see Example 4b).

EXAMPLE 3

(∓)-Vincamine (Compound 4b, R = $C_2H_5$). Diagram I.

The procedure of Example 1 is used, using enamine 1b (R = $C_2H_5$) as starting material. Enamine 1b (360 mg) is dissolved in ethanol-acetonitrile (1:1). After adding methyl α-bromomethyl acrylate (0.7 ml), the reaction medium is refluxed with stirring, under a nitrogen atmosphere, during 20 hours. The reaction mixture is then made alkaline and sodium borohydride is added to the cooled reaction mixture (ice-bath) until complete reduction of the immonium salt (2b, R = $C_2H_5$) (ascertained by thin layer chromatography). The material is poured into water and extracted with chloroform. On evaporation, the chloroform phases leave a brown lacquer which is osmylated in the presence of periodic acid, in the same manner as compound 3a. Extraction with chloroform gives a black lacquer (120 mg). (∓)-Vincamine 4b (25 mg) is separated by crystallization from acetone. M.p. = 190°-232°C (fusion - solidification - fusion).

The compound was compared with the naturally occurring material (E. SCHLITTLER, Helv. Chim. Acta, 1953, 36, 2017;M. PLAT and coll., Bull. Soc. Chim. de Fr., 1962, 5, 1082).

The I.R., U.V., mass and N.M.R. spectra and the melting point are identical.

EXAMPLE 4

(DIAGRAM II)

a. 12H, 12bH-1,2,3,4,6,7-hexahydro-1-ethoxycarbonylmethylindolo [2,3-a]quinolizine (Compound 8, intermediate)

Enamine 1a (R = H) (1 g) dissolved in ethyl iodoacetate (3 cc) is stirred under a nitrogen atmosphere, at 110°C, during 4 hours. After cooling, excess reagent is removed by washing with hexane.

The residue containing immonium iodide (9) may be reduced in two different ways:

a. It is dissolved in ethanol (5 ml) and is then reduced with sodium borohydride (120 mg), added portionwise. The reaction mixture is poured into salt water and is extracted with chloroform, to give 1.13 g of crude product.

b. It is taken up into ethanol and is then hydrogenated at ordinary pressure and temperature over 10% palladium-over-charcoal during 3 hours. After filtration and evaporation of the filtrate, the same crude material is obtained as under (a).

The material is purified through a column of alumina with 30 times the weight of adsorbent and eluted with benzene-chloroform (1:1), to give 460 mg (Yield 33%) of derivative (8). M.p. = 160°C (benzene/hexane, 1/1)
Analysis: for $C_{19}H_{24}O_2N_2$:
Calculated, % : C 73.04 H 7.74 O 10.24 N 8.97
Found % : 72.84 7.69 10.19 8.85
U.V. Spectrum (neutral ethanol): 276 (3.564), 284 (3.581), 292 (3.494).
IR Spectrum (Nujol) : 3365 (NH), 1710 (ester)
(CHCl₃) : 3465 (NH), 2860-2805-2655 (Bohlmann's bands), 1725 (ester).
N.M.R. Spectrum : broad signal 8.1 N-H (δ, CDCl₃)
q 4 -O-CH₂-CH₃
broad signal 3.4 H at 21
t 1.1 CH₃-CH₂-O
Mass Spectrum : peaks at m/e 312 (M⁺, 100 %), 311, 283, 267, 239, 224, 197, 184, 170.

b. 1,2,3,5,6,12,13,13a-octahydro-12-oxo-[3,2,1-d]-indolo-[3,2,1-i,j]-pyrido-[1,5]-naphthyridine or 20-deethyl-eburnamonine (Compound 7a)

A solution of the trans-cis derivative 8 (460 mg) in 0.1M sodium ethoxide (30 ml) is stirred at 50°C during 3 hours. The reaction mixture is then poured into salt water and is extracted with chloroform, to give 400 mg of (±) cis-cis derivative (7). (cis-quinolizidine fusion and cis-fusion of rings D/E).

M.p. = 156°C (hexane)

Analysis: $C_{17}H_{18}ON_2$ Calculated %: C 76.66 H 6.81 N 10.52
Found %: 76.39 6.83 10.33
U.V. Spectrum (neutral ethanol): 242.5 (4.238), 267 (3.957), 295 and 303 (3.602).
I.R. Spectrum (CHCl₃ or Nujol) band at 1705 cm⁻¹ (lactam); no Bohlmann's bands.
N.M.R. Spectrum: m 8.4 H at 10
m 4.3 H at 21

Mass Spectrum: peaks at m/e 266 (M⁺, 100%), 265, 237.

Both enantiomers of (±)-20-deethyl-eburnamonine could be isolated after crystallization of the tartrates ((+)paratoluyl-tartaric acid) from methanol to constant optical rotations; there were obtained two bases having the following optical rotations:
$[\alpha]_D^{20}$ CHCl₃ = +104° and −104°

The process described in the present application makes it possible to obtain (±)vincamine whose useful therapeutic properties are well known, and also new vincamine derivatives. Said new derivatives were also found to possess a vasodilatator action, particularly at the cerebral level, and are therapeutically useful to control deficiencies of the cerebral circulation.

Having now described our invention what we claim as new and desire to secure by Letters Patent is:

1. 20-Deethyl-apovincamine, having the formula:

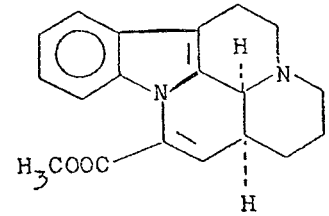

under its racemic and optically active forms.

2. 20-Deethyl-eburnamonine, having the formula:

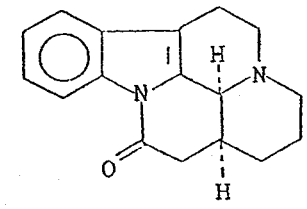

under its racemic and optically active forms.

3. Process for the preparation of compounds having the formula:

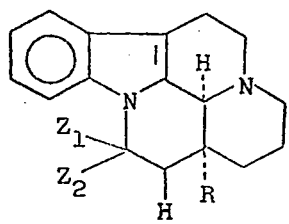

in which, taken together, $Z_1$ and $Z_2$ represent an oxygen atom, and, taken separately, represent one a methoxycarbonyl radical and the other a hydroxy radical and R represents a radical selected from the group consisting of hydrogen and the ethyl group, comprising alkylating an enamine having the formula:

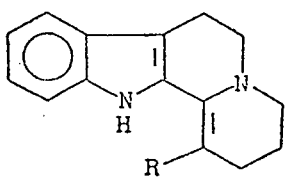

in which R has the above-defined meaning, with methyl α-bromomethyl acrylate, reducing the resulting immonium salt, oxydizing the compound produced which cyclizes simultaneously to give the compound in which $Z_1$ is $COOCH_3$ and $Z_2$ is OH, which is converted, if desired, to the compound in which $Z_1$ and $Z_2$ represent together an oxygen atom.

4. Process as claimed in claim 3, for the preparation of vincamine, comprising alkylating the enamine having the formula:

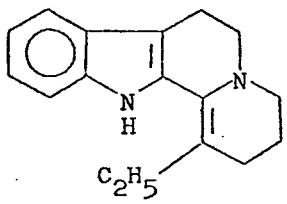

(1b)

with methyl α-bromomethylacrylate, reducing the resulting immonium salt having the formula:

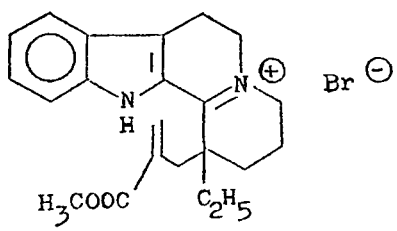

(2b)

with sodium borohydride and then oxidizing the resulting compound

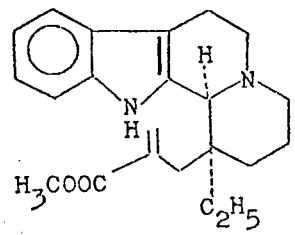

(3b)

with osmium tetraoxide or potassium permanganate in the presence of periodic acid and, cyclization occurring simultaneously, thus obtaining vincamine.

5. Process for the preparation of 20-deethyl-eburnamonine, comprising reacting the enamine having the formula

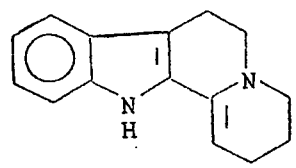

with an ethyl halogeno-acetate, reducing the resulting immonium salt and cyclizing the compound obtained after reduction.

6. A compound having the formula

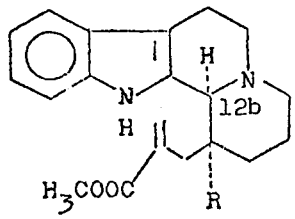

in which R is selected from the group consisting of hydrogen and ethyl.

7. 1,2,3,4,6,7,12,12b-Octahydro-1-ethoxycarbonylmethylindolo[2-3a]-quinolizine having the formula:

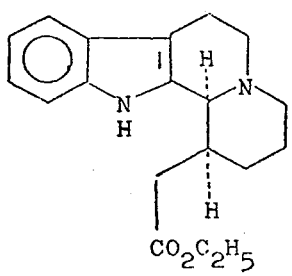

* * * * *